US006585718B2

(12) United States Patent
Hayzelden et al.

(10) Patent No.: US 6,585,718 B2
(45) Date of Patent: Jul. 1, 2003

(54) STEERABLE CATHETER WITH SHAFT SUPPORT SYSTEM FOR RESISTING AXIAL COMPRESSIVE LOADS

(75) Inventors: Robert C. Hayzelden, Canyon Lake, CA (US); John A. Simpson, Carlsbad, CA (US); Wade A. Bowe, Temecula, CA (US); Andrea M. Moore, Murrieta, CA (US); Jesse Flores, Perris, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 74 days.

(21) Appl. No.: 09/848,087

(22) Filed: May 2, 2001

(65) Prior Publication Data

US 2002/0165461 A1 Nov. 7, 2002

(51) Int. Cl.$^7$ .................................................. A61B 1/00
(52) U.S. Cl. ........................ 604/523; 604/524; 604/528; 604/95.04; 138/118
(58) Field of Search ................................ 604/523, 524, 604/525, 526, 527, 528, 95.04; 138/118, 120

(56) References Cited

U.S. PATENT DOCUMENTS

| | | | |
|---|---|---|---|
| 3,521,620 A | 7/1970 | Cook | 600/585 |
| 4,886,067 A | 12/1989 | Palermo | 600/434 |
| 4,921,482 A | 5/1990 | Hammerslag et al. | 604/95.01 |
| 4,979,510 A | 12/1990 | Franz et al. | 600/374 |
| 4,998,916 A | 3/1991 | Hammerslag et al. | 604/528 |
| 5,037,391 A | 8/1991 | Hammerslag et al. | 604/528 |
| 5,106,381 A | 4/1992 | Chikama | 604/528 |
| 5,108,368 A | 4/1992 | Hammerslag et al. | 604/528 |
| 5,125,896 A | 6/1992 | Hojeibane | 604/95.04 |
| 5,176,126 A | 1/1993 | Chikama | 600/139 |
| 5,195,968 A | 3/1993 | Lundquist et al. | 604/95.04 |
| 5,217,465 A | 6/1993 | Steppe | 606/107 |
| 5,228,441 A | 7/1993 | Lundquist | 600/380 |
| 5,231,989 A | 8/1993 | Middleman et al. | 600/434 |
| 5,254,088 A | 10/1993 | Lundquist et al. | 604/95.04 |
| 5,255,668 A | 10/1993 | Umeda | 600/139 |

(List continued on next page.)

FOREIGN PATENT DOCUMENTS

FR 2 713 492 A1 9/1993

OTHER PUBLICATIONS

Grafton A. Smith, M.D. and Edwin L. Brackney, M.D., "Preliminary Report on a New Method of Intestinal Intubation with the Aid of a Flexible Stylet with Controllable Tip," Dept. of Surgery, University of Minnesota Medical School, vol. 27, #6, Jun. 1950, pp. 817–821.

*Primary Examiner*—Patrick Brinson
(74) *Attorney, Agent, or Firm*—Fulwider Patton & Utecht, LLP

(57) ABSTRACT

A catheter includes a steering mechanism for manipulating the distal end of the catheter to obtain a plurality of deflection profiles, a torque transfer system to enhance torque transfer from the handle to the distal tip, and a support system to reduce undesirable deformation of the distal-end region during steering. The torque transfer system includes a flat ribbon within the relatively flexible distal-end region to enhance torque transfer through the distal-end region of the catheter. The support system includes a compression cage and longitudinal struts that are located within the distal-end region of the catheter. The support system can support axial loads and deflect laterally in the direction of the steering, thereby reducing the amount of stretching and compression of the catheter sheath within the deflecting region.

33 Claims, 8 Drawing Sheets

U.S. PATENT DOCUMENTS

| | | | | |
|---|---|---|---|---|
| 5,273,535 | A | 12/1993 | Edwards et al. | 604/95.01 |
| 5,299,559 | A | 4/1994 | Bruce et al. | 600/141 |
| 5,314,418 | A | 5/1994 | Takano et al. | 604/540 |
| 5,315,996 | A | 5/1994 | Lundquist | 600/374 |
| 5,318,525 | A | 6/1994 | West et al. | 604/95.04 |
| 5,318,526 | A | 6/1994 | Cohen | 604/95.04 |
| 5,322,064 | A | 6/1994 | Lundquist | 600/381 |
| 5,325,845 | A | 7/1994 | Adair | 600/114 |
| 5,327,905 | A | 7/1994 | Avitall | 600/585 |
| 5,328,467 | A | 7/1994 | Edwards et al. | 604/95.01 |
| 5,329,923 | A | 7/1994 | Lundquist | 600/373 |
| 5,334,145 | A | 8/1994 | Lundquist et al. | 604/95.04 |
| 5,336,182 | A | 8/1994 | Lundquist et al. | 600/528 |
| 5,358,478 | A | 10/1994 | Thompson et al. | 604/95.04 |
| 5,358,479 | A | 10/1994 | Wilson | 604/95.04 |
| 5,363,861 | A | 11/1994 | Edwards et al. | 600/585 |
| 5,372,587 | A | 12/1994 | Hammerslag et al. | 604/95.04 |
| 5,381,782 | A | 1/1995 | DeLaRama et al. | 600/149 |
| 5,383,852 | A | 1/1995 | Stevens-Wright | 604/95.04 |
| 5,383,923 | A | 1/1995 | Webster, Jr. | 607/125 |
| 5,395,327 | A | 3/1995 | Lundquist et al. | 604/528 |
| 5,431,168 | A | 7/1995 | Webster, Jr. | 600/435 |
| 5,454,787 | A | 10/1995 | Lundquist | 604/95.01 |
| 5,478,330 | A | 12/1995 | Imran et al. | 604/526 |
| 5,487,757 | A | 1/1996 | Truckai et al. | 604/264 |
| 5,489,270 | A | 2/1996 | van Erp | 604/95.04 |
| 5,496,260 | A | 3/1996 | Krauter et al. | 600/148 |
| 5,507,725 | A | 4/1996 | Savage et al. | 604/95.04 |
| 5,531,686 | A | 7/1996 | Lundquist et al. | 604/95.04 |
| 5,545,200 | A | 8/1996 | West et al. | 607/122 |
| 5,599,305 | A | 2/1997 | Hermann et al. | 604/95.04 |
| 5,642,736 | A | 7/1997 | Avitall | 600/585 |
| 5,674,197 | A | 10/1997 | van Muiden et al. | 604/95.04 |
| 5,676,653 | A | 10/1997 | Taylor et al. | 604/45.04 |
| 5,687,723 | A | 11/1997 | Avitall | 600/374 |
| 5,755,731 | A | 5/1998 | Grinberg | 606/170 |
| 5,755,760 | A | 5/1998 | Maguire et al. | 607/122 |
| 5,782,828 | A | 7/1998 | Chen et al. | 606/42 |
| 5,797,842 | A | 8/1998 | Pumares et al. | 600/435 |
| 5,810,802 | A | 9/1998 | Panescu et al. | 606/31 |
| 5,827,242 | A | 10/1998 | Follmer et al. | 604/526 |
| 6,033,394 | A | 3/2000 | Vidlund et al. | 604/524 |
| 6,045,550 | A * | 4/2000 | Simpson et al. | 600/549 |
| 6,049,737 | A * | 4/2000 | Simpson et al. | 607/119 |
| 6,063,077 | A | 5/2000 | Schaer | 606/41 |
| 6,142,994 | A | 11/2000 | Swanson et al. | 606/41 |
| 6,146,338 | A | 11/2000 | Gardeski et al. | 604/584 |
| 6,163,716 | A | 12/2000 | Edwards et al. | 600/374 |
| 6,208,881 | B1 | 3/2001 | Champeau | 600/374 |

\* cited by examiner

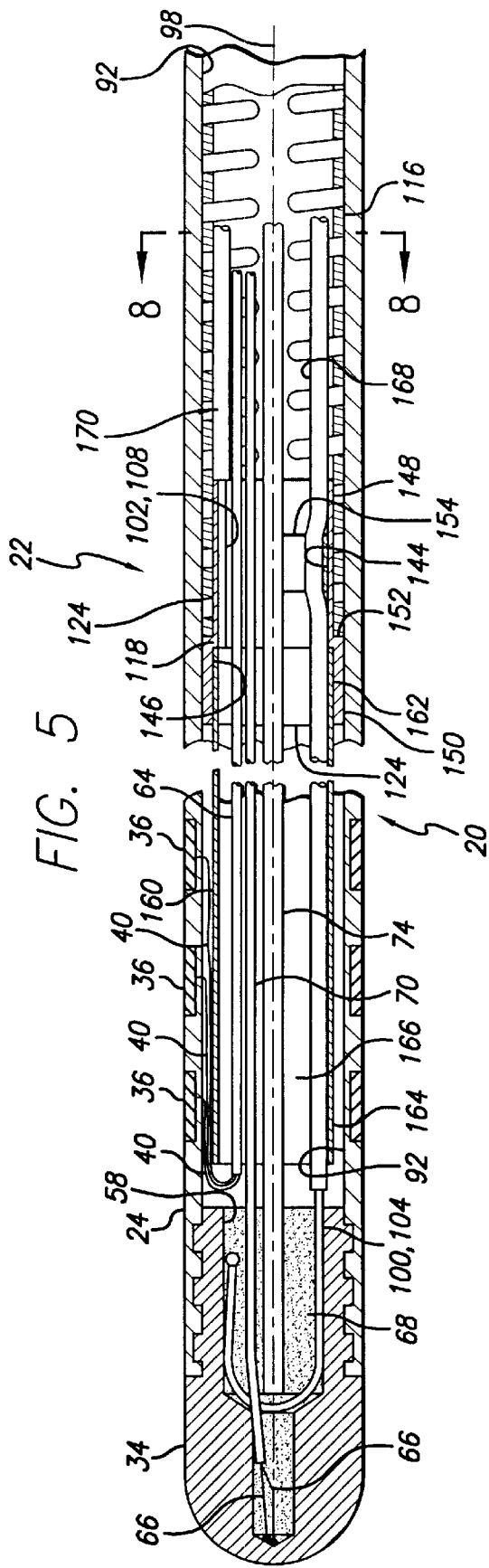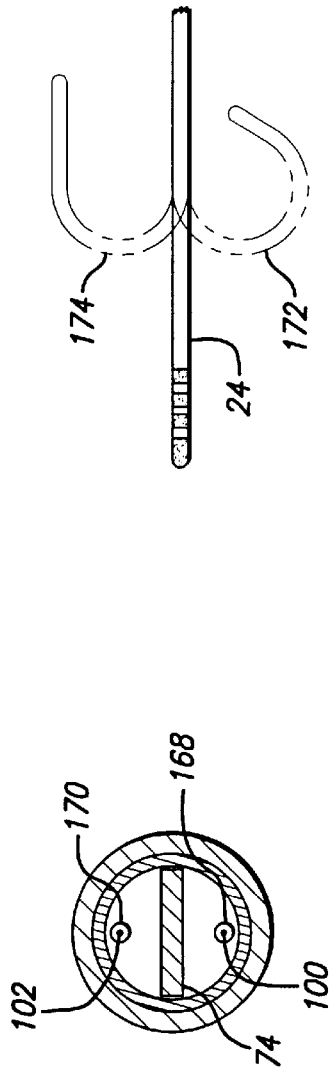

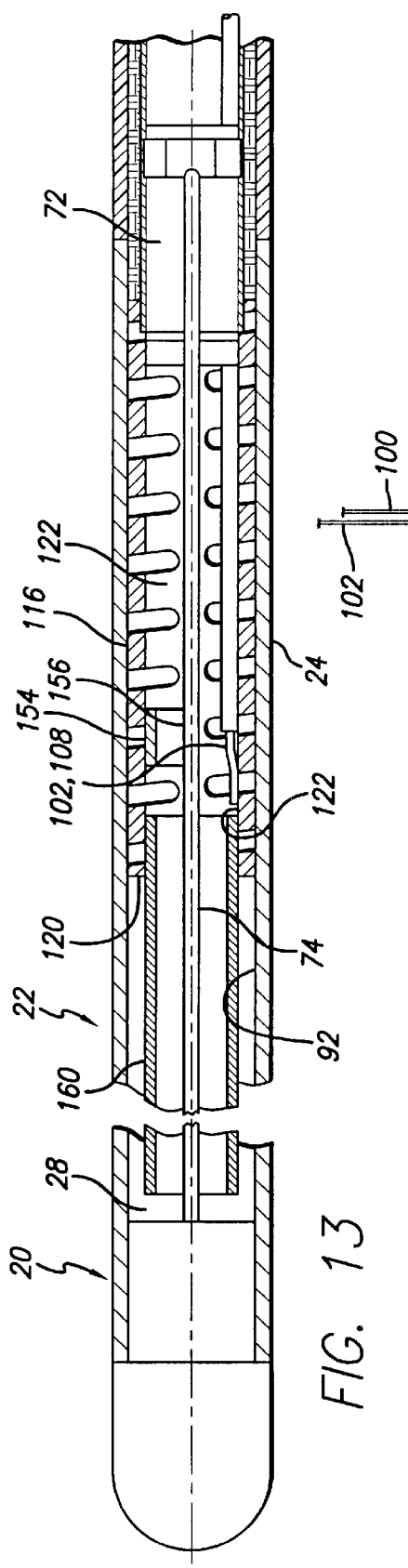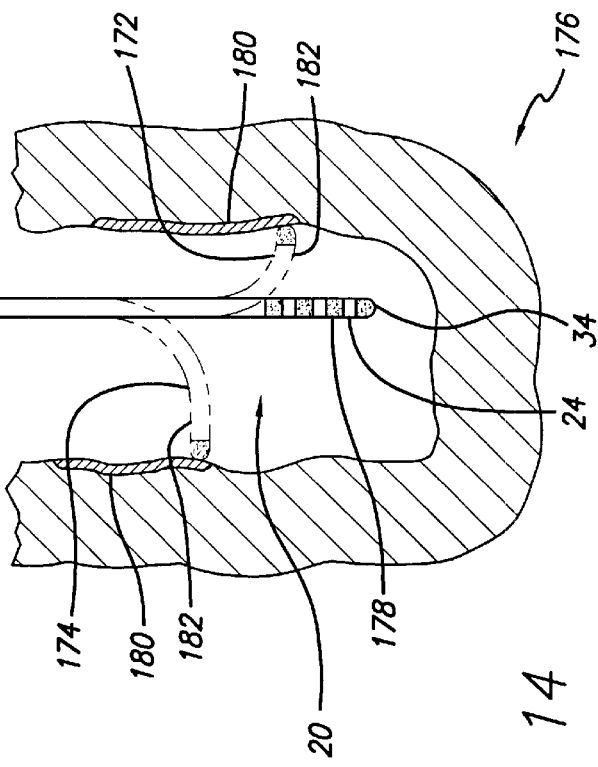

STEERABLE CATHETER WITH SHAFT SUPPORT SYSTEM FOR RESISTING AXIAL COMPRESSIVE LOADS

BACKGROUND OF THE INVENTION

The invention relates generally to catheters, and more particularly to a catheter having a steerable distal-end region with a shaft support system for resisting axial compressive loads.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery or vein to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate electrophysiological ("EP") catheter system.

One such EP catheter system, as disclosed in U.S. Pat. Nos. 6,059,778 and 6,096,036, includes a plurality of spaced apart band electrodes located at the distal end of the catheter and arranged in a linear array. The band electrodes are positioned proximal heart tissue. RF energy is applied through the electrodes to the heart tissue to produce a series of long linear lesions similar to those produced by the Maze procedure. The catheters currently used for this procedure are typically flexible at the distal end, and the profile at the distal end is adjustable. However, when using such catheters, it is often difficult to conform the distal-end profile to some of the irregular topographies of the interior cavities of the heart. In other instances, it is difficult for a multi-electrode catheter that is designed to produce long linear lesions to access and ablate tissue in regions that require short linear lesions, such as the so-called isthmus region that runs from the tricuspid annulus to the eustachian ridge. Ablation of tissue in this region, and other regions non-conducive to the placement of multi-electrode, long, linear-lesion ablation catheters within them, is best accomplished by delivering RF energy to a tip electrode to produce localized spot lesions or if longer lesions are required, by energizing the tip while it is moved across the tissue.

Other catheters for producing spot lesions or tip-drag lesions typically include a tip ablation electrode and a plurality of mapping band electrodes positioned at the distal end of the catheter. The catheters are steerable in that they are configured to allow the profile of the distal end of the catheter to be manipulated from a location outside the patient's body. Steerable catheters that produce multiple deflection profiles of their distal ends provide a broader range of steerability. However, known steerable catheters, such as that disclosed in U.S. Pat. No. 5,195,968, have steering tendons attached to a ribbon at or near the longitudinal centerline of the catheter. Because of the relatively short distance between the tendon attachment point and the ribbon that resides along the centerline of the catheter sheath, a force applied to the tendon results in a relatively small bending moment for deflecting the distal tip. The ribbon/tendon assembly is typically provided clearance to allow the tendon to become substantially displaced from the centerline as deflection progresses, thereby enlarging the moment arm and consequently increasing the applied bending moment. Unfortunately, this requires such designs to include additional lumen space, translating into larger catheter diameters. Larger diameter catheters are undesirable due to the increased trauma they inflict on a patient. Further, as the tendon displaces to the extent that it contacts the catheter wall, the associated friction may necessitate greater exertion to further deflect the distal tip. Lessening the amount of force required to deflect the distal tip of a catheter by actions outside the catheter is desired in that the catheter tip can more easily be deflected and placed in the correct location within a patient.

In some catheters that have a ribbon within the distal-end region and a steering tendon affixed to the sheath at a point proximal the distal tip within the distal-end region, undesirable deformation of the sheath can occur when the steering tendon is axially displaced in the proximal direction. More specifically, as the steering tendon is axially displaced in the proximal direction, the portion of the sheath in the distal-end region proximal the attachment point compresses, thus causing the sheath to wrinkle, and the portion of the sheath distal the attachment point stretches. Such deformation of the sheath can lead to fluid ingress beneath the catheter's band electrodes or can cause damage to internal wires or mechanical components.

Hence, those skilled in the art have identified a need for a tip-electrode, ablation catheter with a steerable distal-end region that resists deformation even after repeated steering. The present invention fulfills these needs and others.

SUMMARY OF THE INVENTION

Briefly, and in general terms, the present invention is directed to a catheter with a steerable distal-end region and a shaft support system for resisting axial compressive loads.

In a first aspect, the invention relates to a catheter that includes a sheath having a proximal region, a distal-end region, and a longitudinal centerline. The catheter also includes at least one steering tendon that is housed within the sheath. The at least one steering tendon has a first end that is attached to the distal-end region of the sheath, and a second end that is located at the proximal region of the sheath. Movement of the at least one steering tendon in a proximal direction causes the sheath distal-end region to deflect. The catheter also includes a support system having a proximal end, a distal end and a lumen there between. The support system is sized to fit within the distal-end region of the sheath and is configured to deflect laterally relative to the centerline and to resist axial compression along the centerline.

In a detailed aspect of the invention, the support system includes a helical coil that defines the lumen and at least one strut that is secured to one side of the coil along the length of the coil. In another aspect, the support system includes a pair of struts secured to diametrically opposite sides of the coil. In a further aspect, the support system is formed of a resiliently deformable, shape-memory material. In another detailed facet of the invention, the support system includes a linear array of hollow rings that defines the lumen, and at least one strut that is secured to one side of each of the rings. In a further facet, the support system includes a pair of struts that are secured to diametrically opposite sides of each of the rings. In another detailed aspect of the invention, the support system includes a substantially tubular member with an array of notches. In a more detailed aspect, the notches are diametrically opposite and offset from each other. In another detailed facet of the invention, the catheter includes a ribbon isolation sleeve that has a proximal end attached to the distal-end of the support system. In a further facet, the ribbon isolation sleeve is formed of a resiliently deformable material. In a more detailed facet the ribbon isolation sleeve includes a wire coil embedded within the material. In yet another detailed aspect of the invention, the first end of the at least one steering tendon is attached at a location offset from the centerline of the sheath.

In a second aspect, the invention relates to a catheter that includes a sheath having a proximal region and a distal-end region. The catheter also includes a first steering tendon that is housed within the sheath. The first steering tendon has a first end that is attached to the distal-end region at a point proximate an inner surface of the sheath, and a second end that exits a proximal end of the sheath. Movement of the first steering tendon in a proximal direction causes the sheath distal-end region to deflect. The catheter also includes a second steering tendon that is housed within the sheath. The second steering tendon has a first end and a second end. The first end of the second steering tendon is attached to the distal-end region at a point proximate the inner surface of the sheath and proximal the attachment point of the first steering tendon. The second end of the second steering tendon has a second end that exits the proximal end of the sheath. Movement of the second steering tendon in the proximal direction causes the sheath distal-end region to deflect. The catheter also includes a compression cage that has a proximal end, a distal end and a lumen there between. The compression cage is sized to fit within the distal-end region of the sheath and is configured to deflect laterally and to support an axial load.

In a detailed aspect of the invention, the first end of the second steering tendon is coupled to the compression cage. In a more detailed aspect, the first end of the second steering tendon attaches to a distal portion of the compression cage. In another detailed facet of the invention, the catheter also includes an anchor band that is attached to the distal end of the compression cage. In another facet, the first end of the second steering tendon is attached to the anchor band. In another detailed aspect of the invention, the catheter also includes a torque transfer system that is housed within the compression cage and is adapted to transfer torsional forces from the proximal region of the sheath to the distal-end region of the sheath. In a more detailed aspect, the torque transfer system includes an eyelet that is secured at the distal end of the proximal region of the sheath and the proximal end of the compression cage is secured to the eyelet. In another detailed aspect, the torque transfer system further includes a ribbon that is housed within the compression cage and is configured to deflect therewith. The ribbon has a first end that is secured within the eyelet and a second end that is attached to the distal-end region of the sheath. In a further detailed aspect, the ribbon is positioned along the centerline of the distal-end region of the sheath. In an additional aspect, the ribbon is formed of a resiliently deformable, shape-memory material. In a still further aspect, the ribbon has a substantially rectangular cross-section. In yet another aspect, the compression cage and the ribbon are each adapted to deflect in a direction, and the compression cage further includes a ribbon locator that is adapted to align the deflecting direction of the compression cage with the deflecting direction of the ribbon.

In a third aspect, the invention relates to a catheter for use with biological tissue that includes a sheath having a proximal region and a distal-end region. The catheter also includes at least one electrode that is located in the distal-end region for transferring energy to the biological tissue. The catheter further includes a first steering tendon that is housed within the sheath. The first steering tendon has a first end that is attached to the distal-end region at a point proximate an inner surface of the sheath, and a second end that exits a proximal end of the sheath. Movement of the first steering tendon in a proximal direction causes the sheath distal-end region to deflect. The catheter also has a second steering tendon that is housed within the sheath. The second steering tendon has a first end and a second end. The first end of the second steering tendon is attached to the distal-end region at a point proximate the inner surface of the sheath and proximal the attachment point of the first steering tendon. The second end of the second steering tendon exits the proximal end of the sheath. Movement of the second steering tendon in the proximal direction causes the sheath distal-end region to deflect. The catheter also includes a compression cage that has a proximal end, a distal end and a lumen there between. The compression cage is sized to fit within the distal-end region of the sheath and is configured to deflect laterally therewith and to resist axial compression. The catheter further includes a torque transfer system that is housed within the compression cage and is adapted to transfer torsional forces from the proximal region of the sheath to the distal-end region of the sheath.

In a detailed aspect of the invention, the first steering tendon is secured within a distal tip of the sheath. In another aspect, the at least one electrode includes a tip electrode that is located at the distal end of the sheath, and the first steering tendon is secured within the tip electrode. In another detailed facet of the invention, the compression cage includes a helical coil that defines the lumen, and at least one strut that is secured to one side of the coil along the length of the coil. In a more detailed facet, the catheter also includes an anchor band that has a proximal end and a distal end with a central lumen there between. The anchor band is housed within the distal-end region, and the proximal end of the anchor band is attached to the distal end of the compression cage. In a further facet, the first end of the second steering tendon is attached to the anchor band.

These and other aspects and advantages of the invention will become apparent from the following detailed description and the accompanying drawings, which illustrate by way of example the features of the invention.

BRIEF DESCRIPTION OF THE DRAWINGS

FIG. 5 is a cross-sectional plan view of the distal-end region of the catheter of FIG. 1 depicting the attachment points for the steering tendons, wherein the steering tendons are disposed approximately 180° apart and on opposite sides of the torque transfer system;

FIG. 8 is a cross-section view of the distal-end region depicting the steering tendons disposed approximately 180° apart and on opposite sides of the torque transfer system, taken along the line 8—8 from FIG. 5 with other items removed for clarity;

FIG. 9 is a schematic depicting the profiles that may be created within the distal-end region of the catheter of FIG. 5 when the first steering tendon and the second steering tendon are axially displaced in a proximal direction;

FIG. 13 is a cross-sectional plan view of the distal-end region of another configuration of the catheter of FIG. 1 depicting the second steering tendon attached to the inner surface of the support system; and FIG. 14 is a schematic depicting the catheter of FIG. 1 in use in a biological cavity within a patient.

DETAILED DESCRIPTION OF THE PREFERRED EMBODIMENTS

Figure 1:
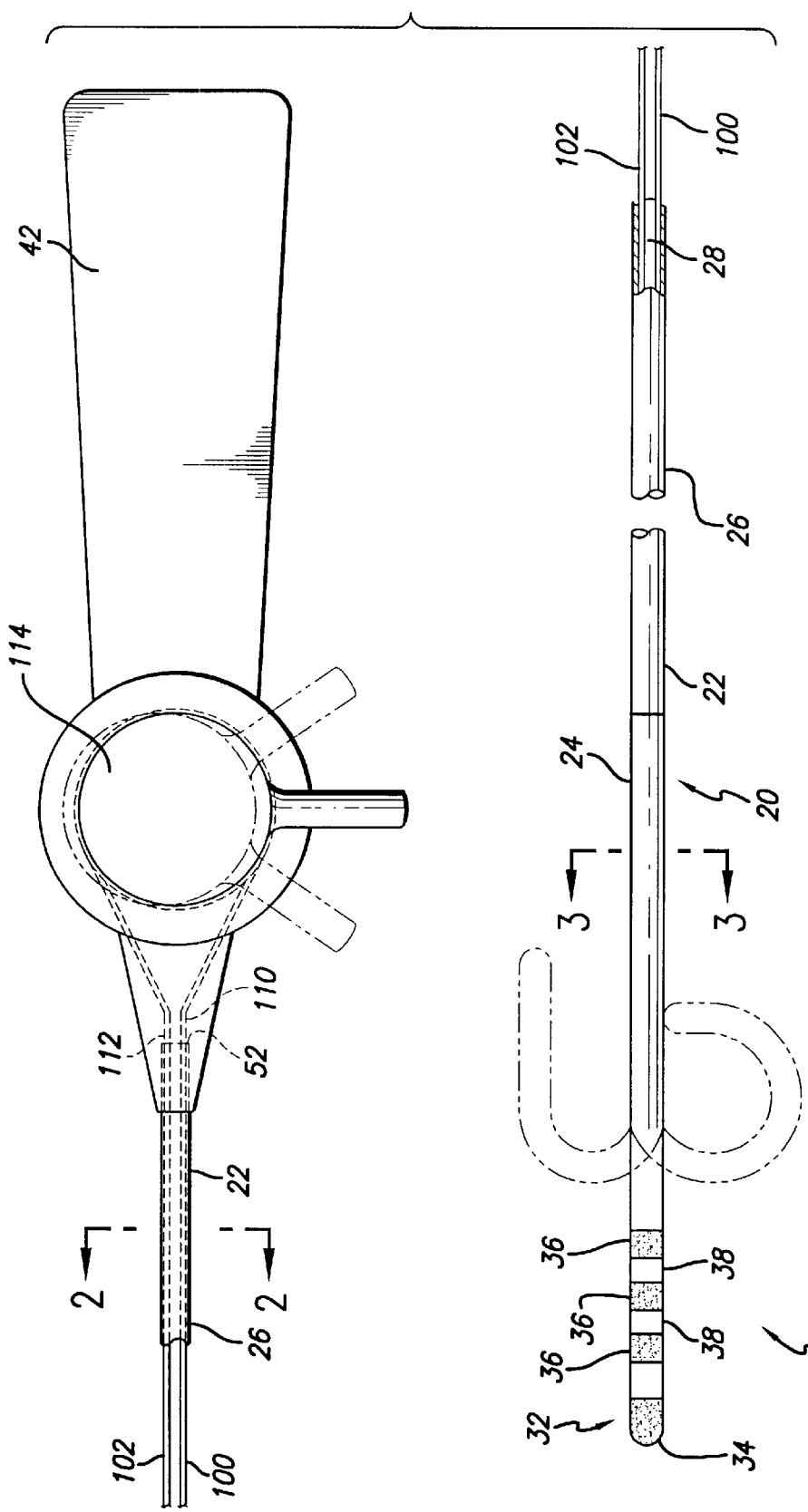
FIG. 1 is a plan view with a broken-out section of a catheter configured in accordance with aspects of the invention and depicting components of the catheter including a sheath, a steering mechanism and a steering handle.

Referring now to the drawings, in which like reference numerals are used to designate like or corresponding elements among the several figures, in FIG. 1 there is shown a catheter 20 incorporating aspects of the present invention. The catheter 20 includes a sheath 22 having a flexible distal-end region 24, a proximal region 26 and an open lumen 28 running throughout. At the distal end 30 of the distal-end region 24 is a distal tip 32. The distal-end region 24 includes a tip electrode 34 for applying ablation energy to a biological site. Located proximal from the tip electrode 34 are three band electrodes 36 arranged in a substantially linear array along the distal-end region 24 of the sheath 22. The band electrodes 36 are arranged so that there is space 38 between adjacent electrodes. In one configuration, the band electrodes 36 are two mm wide and the space 38 between the electrodes is also two mm wide. Alternatively, the band electrodes 36 may be three mm wide and the space 38 between the electrodes may be four mm wide, or any other dimensions suitable for mapping and/or ablation procedures. The band electrodes 36 may be used to map the interior surfaces of the heart or to apply ablation energy, or both. The tip electrode 34 may be used to deliver RF energy to the biological site to form spot or tip-drag lesions, or for mapping, or for both. Individual lead wires 40 (not shown in FIG. 1) run from the handle 42 to each band electrode 36.

Figure 2:
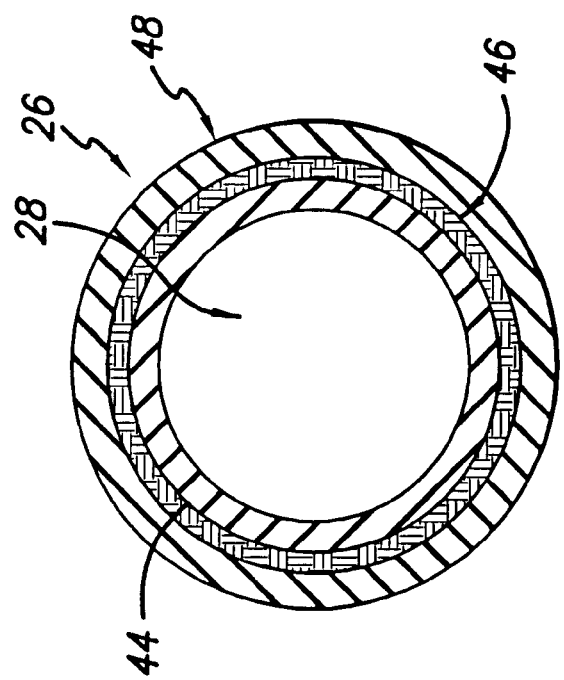
FIG. 2 is a cross-section view of the construction of the proximal region of the sheath taken along the line 2—2 from FIG. 1.

With reference to FIG. 2, which is a cross-sectional view taken from FIG. 1, the proximal region 26 of the sheath 22 is a layered composite. The inner layer 44 is a hollow tube made of a polymer possessing a high modulus of elasticity, such as polyetheretherketone (PEEK). A middle layer 46 having one or more layers of braided, 0.025 mm×0.075 mm stainless steel ribbons is applied upon the inner layer 44 to increase the torque transfer strength of the proximal region 26. Only one layer is shown in FIG. 2 for clarity of illustration. The proximal region's 26 outer layer 48 is made of a flexible, intermediate-durometer polymer such as polyether block amide, known commercially as Pebax™. In one embodiment, the outer layer 48 includes a 63D (Shore "D" hardness scale) hardness scale Pebax™ tube. The three layers 44, 46, and 48 are bonded together by the simultaneous application of heat and pressure, thus creating a flexible tube with the braided stainless steel ribbons of the middle layer 46 providing superior torsional rigidity.

Figure 3:
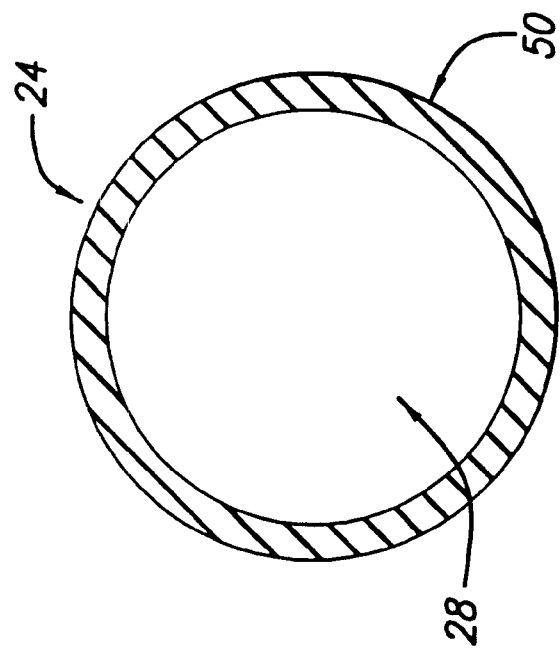
FIG. 3 is a cross-section view of the construction of the distal-end region of the sheath taken along the line 3—3 from FIG. 1.

With reference to FIG. 3, which is a cross-sectional view taken from FIG. 1, the construction of the distal-end region 24 includes a single layer 50 of a lower durometer Pebax™. In one embodiment, the layer 50 includes a 35D (Shore "D" hardness scale) hardness scale Pebax™ tube. Accordingly, the distal-end region 24 is more flexible and has lower torque transfer strength than the proximal region 26. To further increase flexibility, the distal-end region 24 of the sheath 22 may have a lower durometer material or a thinner wall.

Figure 4:
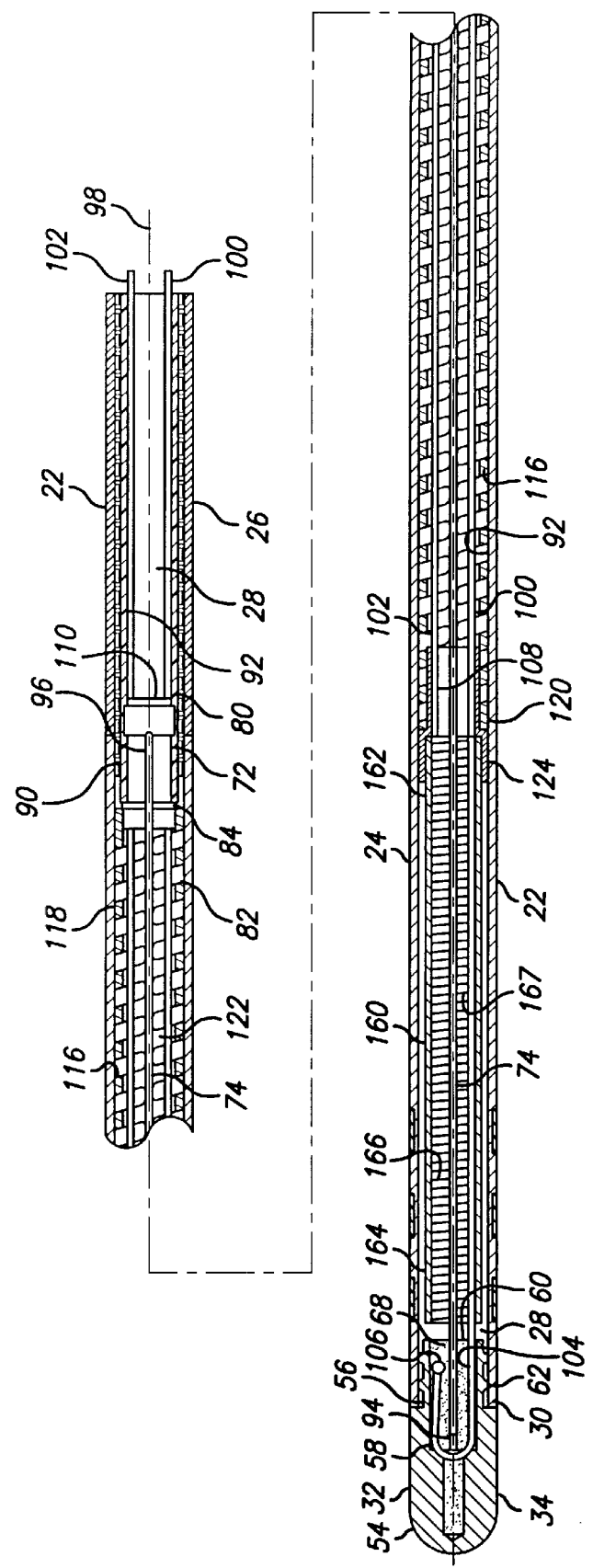
FIG. 4 is a cross-sectional plan view with a broken-out section of the distal portion of the catheter of FIG. 1 depicting detailed components including steering tendons arranged to provide bidirectional steering profile capabilities, a torque transfer system, and a support system.

Referring to FIG. 4, the distal ends of the three layers 44, 46 and 48 are stepped, thus exposing the outer surface of the inner layer and the braided stainless steel ribbons of the middle layer. A proximal portion of the distal-end region 24 of the sheath 22 overlaps the exposed portion of the middle layer 46 of the proximal region 26 and butts against the distal end of the outer layer 48 of the proximal region. The proximal portion of the distal-end region 24 is then bonded to the distal portion of the proximal region 26 to form one continuous sheath 22 through techniques that are well known to those skilled in the art, such as with epoxy. The proximal end 52 of the sheath 22 is bonded to the handle 42 (FIG. 1), such as with cyanoacrylate adhesive, or attached by some equivalent mechanical means.

With continuing reference to FIG. 4, the tip electrode 34 includes a substantially domeshaped distal portion 54 and a substantially cylindrical proximal portion 56. The two portions 54, 56 are contiguous and are preferably formed as a single unitary structure. The tip electrode 34 includes a bore 58 that penetrates the proximal surface 60 of the proximal portion 56. The proximal portion 56 also includes raised ridges 62 to aid in anchoring the tip electrode 34 to the sheath 22. The tip electrode 34 is formed from a biocompatible material having high thermal conductivity properties. Possible materials include silver, gold, chromium, aluminum, molybdenum, tungsten, nickel, platinum, and platinum/10% iridium.

With reference to FIG. 5, lead wires 40 are attached to the band electrodes 36 in a way that establishes good electrical contact, such as by welding. The lead wires 40 are grouped together and enclosed within a sheath 64 that spans throughout the distal-end region 24 and continues into the proximal region 26 of the sheath 22. The sheath 64 is formed of a flexible material, such as a thin-walled heat-shrink tubing, so that it may deflect when needed.

With further reference to FIG. 5, a pair of thermocouple wires 66 run from the handle 42 shown in FIG. 1 through the sheath 22 to the bore 58 within the tip electrode 34. Each of the thermocouple wires 66 is individually attached at the distal end of the bore 58 in the tip electrode 34 in a way that achieves good electrical contact, such as by soldering. By attaching the thermocouple wires 66 to the tip electrode 34 in this manner, the thermocouple effect is achieved through the tip electrode, and good thermal contact is achieved for a more accurate determination of the temperature of the tip electrode. After being attached to the bore 58, the thermocouple wires 66 are potted into the bore with a resin 68, such as epoxy. One of the thermocouple wires 66 also serves as a drive wire to transmit ablation energy to the tip electrode 34. Exemplary configurations of electrodes having combination thermocouple/drive wires are disclosed in U.S. Pat. Nos. 6,049,737 and 6,045,550. The thermocouple wires 66 are grouped together and enclosed within a sheath 70 that spans throughout the distal-end region 24 and continues into the proximal region 26 of the sheath 22. The sheath 70 is formed of a flexible material, such as a thin-walled heat-shrink tubing, so that it may deflect when needed. In an alternate embodiment, the thermocouple wires are twisted and soldered together prior to being soldered into the tip electrode. While the thermocouple effect in this configuration does not depend on the tip electrode, the attachment of the thermocouple to the tip electrode does provide the wire pair with good thermal contact.

Figure 6:
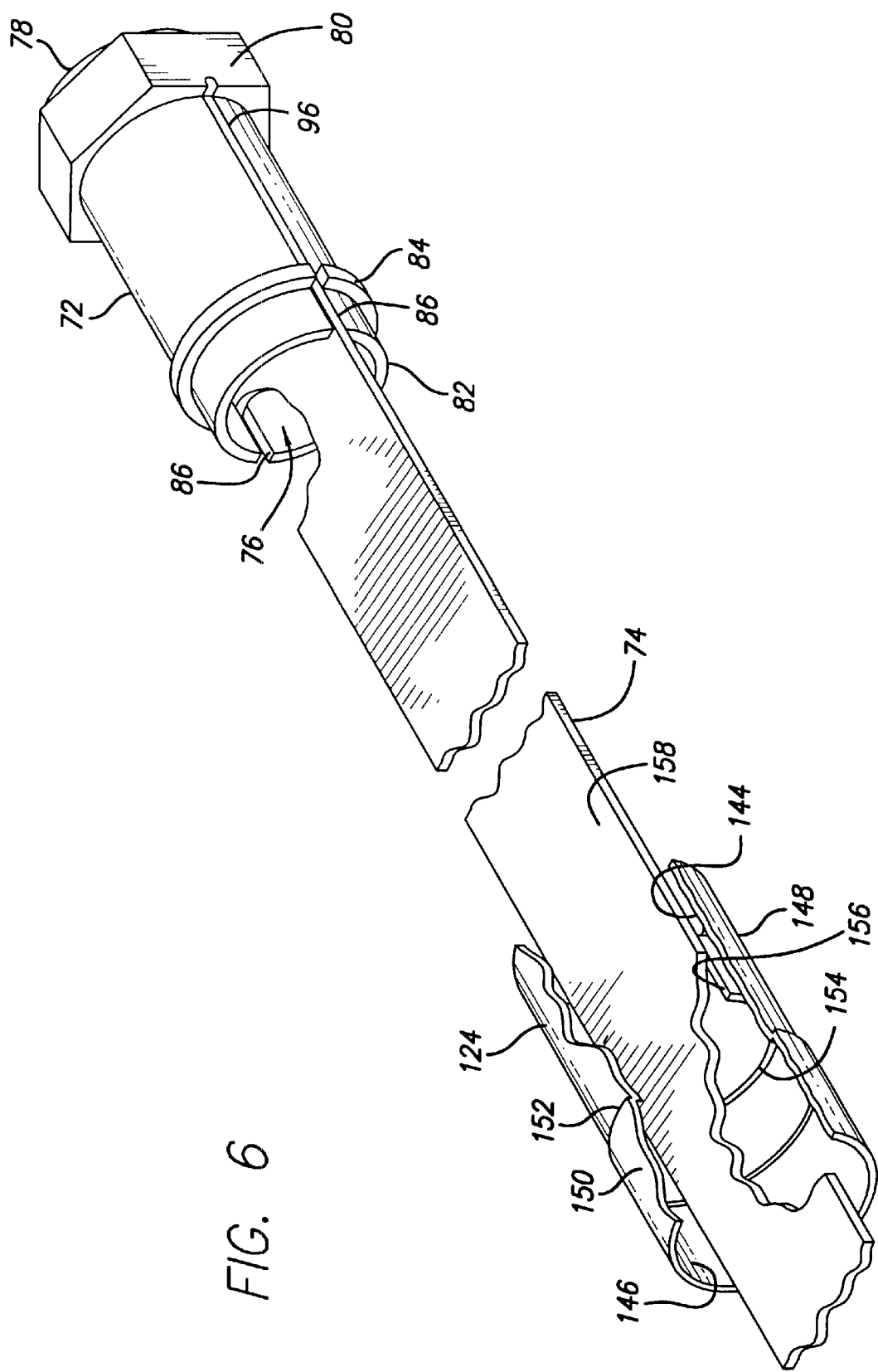
FIG. 6 is a tri-metric view with a broken-out section of the catheter of FIG. 1 depicting the detailed components of the torque transfer system including an eyelet, a flat ribbon and an anchor band with other items removed for clarity.
Figure 7A:
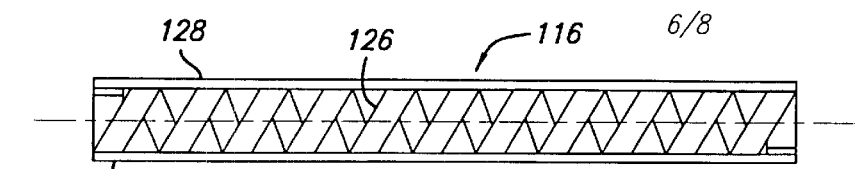
FIG. 7A is a view of a support system comprised of a flat-wire coil and struts.
Figure 7B:
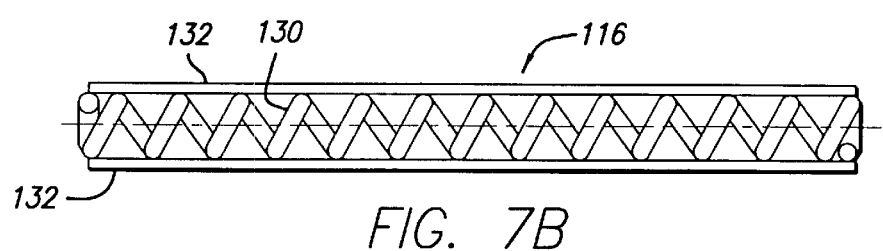
FIG. 7B is a view of a support system comprised of a round-wire coil and struts.
Figure 7C:
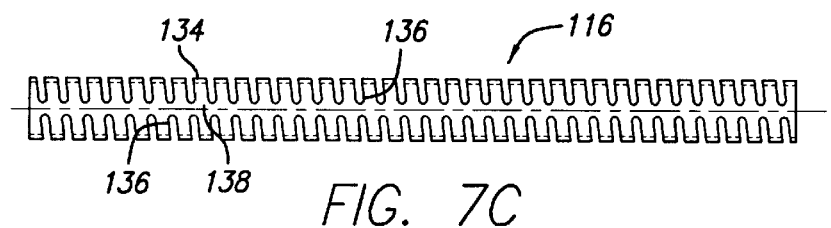
FIG. 7C is a view of a support system comprised of a tubular member with an array of deep notches.
Figure 7D:
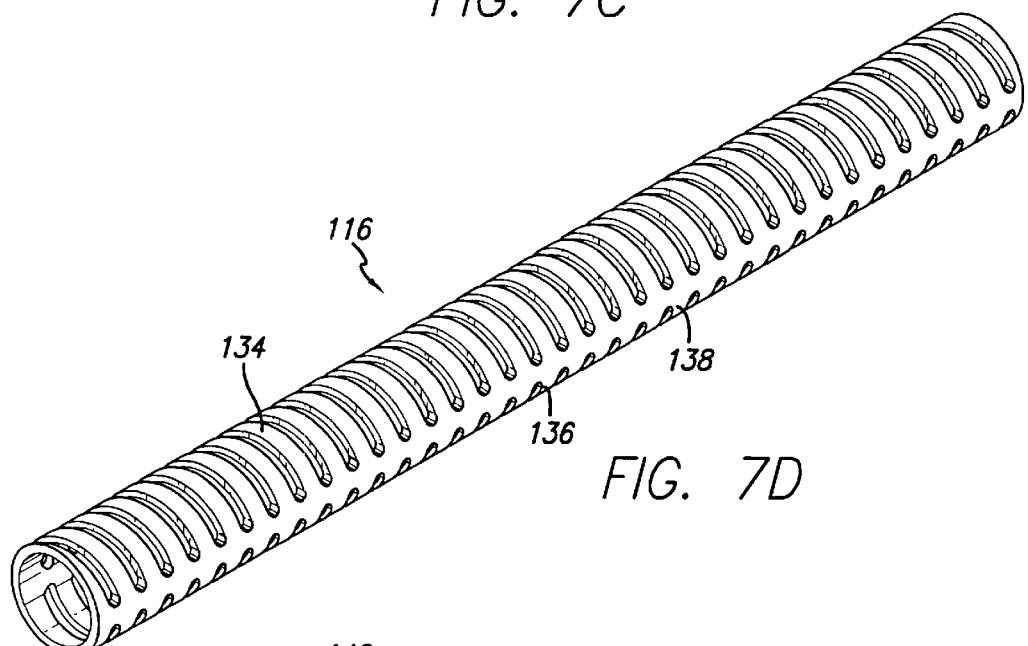
FIG. 7D is a perspective view of the support system of FIG. 7C.
Figure 7E:
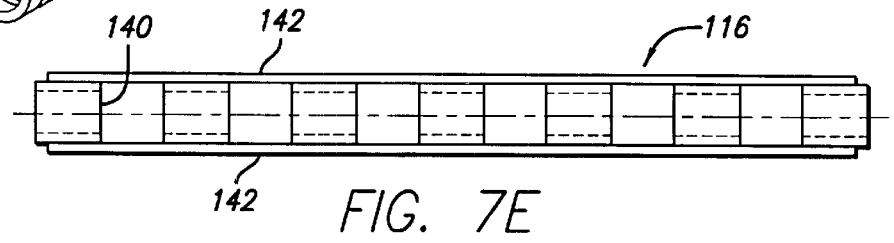
FIG. 7E is a view of a support system comprised of a linear array of hollow rings connected with struts.

Referring again to FIG. 4 and to FIG. 6, a torque transfer system that includes an eyelet 72 and a flat ribbon 74 is housed within the sheath 22. The torque transfer system is adapted to increase the torque transfer strength of the distal-end region 24 and to facilitate the transfer of torsional forces from the proximal region 26 of the sheath 22 to the distal-end region 24 of the sheath. The eyelet 72 is tubular in shape and includes a central lumen 76. A proximal end 78 of the eyelet 72 includes an enlarged, non-circular flange 80 with a substantially angular shape, such as a hexagon. The non-circular flange 80 has a cross-sectional diameter that is greater than the inner diameter of the sheath 22. Near the distal end 82 of the eyelet 72 is a circular flange 84 that protrudes outwardly. Extending through the distal end 82 of the eyelet 72 is a pair of longitudinal, diametrically opposed slots 86. The eyelet 72 is preferably made from a metallic material, such as stainless steel. The eyelet 72 is installed into the central lumen 28 of the sheath 22, prior to the joining of the distal-end region 24 and the proximal region 26, by inserting the proximal end 78 of the eyelet into the distal end 90 of the proximal region of the sheath until the circular flange 84 butts against the distal end of the proximal region. Such installation secures the non-circular flange 80 of the eyelet 72 within the sheath 22 by embedding itself into the inner surface 92 of the proximal region 26 of the sheath.

Figure 10:
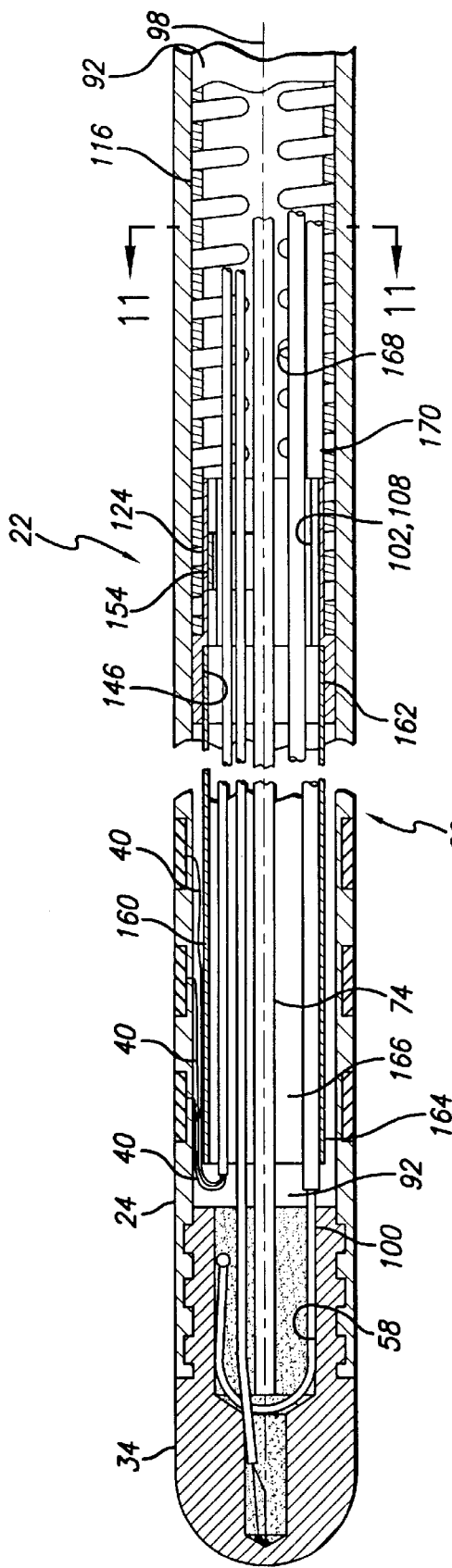
FIG. 10 is a cross-sectional plan view of the distal-end region of another configuration of the catheter of FIG. 1 depicting the attachment points for the steering tendons, wherein the steering tendons are disposed approximately angularly aligned.

With continued reference to FIGS. 4 and 6, the flat ribbon 74 includes a distal end 94 and a proximal end 96, and is preferably made from a resiliently deformable, shape-memory material, such as Nitinol. Such material permits the flat ribbon 74 to deflect with the distal-end region 24 of the sheath 22, yet the shape-memory aspect of the flat ribbon tends to return the flat ribbon, and also the catheter distal end, to the straight, or non-deflected, shape as shown in FIGS. 5 and 10. In one embodiment, the flat ribbon 74 includes a flattened Nitinol wire and has a substantially rectangular cross section with a width that is substantially greater than its thickness. In this way, the flat ribbon 74 bends most easily in the direction of its smallest bending stiffness, which is in a direction perpendicular to its width. The distal end 94 of the flat ribbon 74 is attached to the distal-end region 24 of the sheath 22 and the proximal end 96 of the flat ribbon is attached to the proximal region 26 of the sheath. More specifically, the proximal end 96 of the flat ribbon 74 is installed through the distal end 30 of the distal-end region 24, inserted into the slots 86 within the eyelet 72, and bonded into place, such as with epoxy, or attached by an equivalent mechanical means. Further, lateral movement of the proximal end 96 of the flat ribbon 74 is restricted by the inner surface 92 of the sheath 22. The distal end 94 of the flat ribbon 74 is installed into the bore 58 of the distal tip 32 and is bonded into place with the resin 68. In this fashion, the flat ribbon 74 bridges the entire distal-end region 24 between the proximal region 26 and the distal tip 32. Such installation positions the flat ribbon 74 along the centerline 98 of the distal-end region 24 of the sheath 22.

The torsional rigidity of the distal-end region 24 is significantly enhanced by the installation of the flat ribbon 74. As a result, rotations of the handle 42 (FIG. 1) by the operator are accurately transferred to the distal tip 32. More specifically, as the handle 42 is rotated, the torsional forces that are exerted transfer to the proximal region 26 of the sheath 22 because of the attachment means between the handle and the sheath. The braided stainless steel ribbons of the middle layer 46 (FIGS. 2 and 4) within the proximal region 26 transfers the torsional forces to the distal end 90 of the proximal region of the sheath 22. The torsional forces are then transferred to the eyelet 72 (FIGS. 4 and 6) by means of the non-circular flange 80 that is embedded within the distal end 90 of the proximal region 26. Since the embedded portion of the eyelet 72 is non-circular, the eyelet will not rotate freely within the proximal region 26 of the sheath 22. Therefore, the torsional forces are transferred from the eyelet 72 to the flat ribbon 74 (FIGS. 4 and 6) whose proximal end 96 is interrelated with the slots 86 in the eyelet. Since the distal end 94 of the flat ribbon 74 is bonded into the bore 58 of the distal tip 32 (FIG. 4), the torsional forces are transferred to the distal tip. With the enhanced distal torque transfer provided by the flat ribbon 74, the torque imparted by the proximal region 26 is effectively transferred to the distal tip 32 without the need for a middle layer of braided material within the distal-end region 24, such as the middle layer 46 of the proximal region. As is well known, additional layers increase stiffness, size, and cost. A significant advantage of the torque transfer system using the flat ribbon 74 is that rotational handle 42 movements will be accurately transferred to the distal tip 32. Thus, the operator can place the distal tip 32 of the catheter 20 at a desired location within a patient with greater precision and the possibility of harm to the patient due to an uncontrolled "whipping" type movement of the distal region is sharply reduced. Another advantage of having the flat ribbon 74 within the distal-end region 24 is that by rotating the handle 42 with the distal-end region in the deflected condition, the distal tip 32 can exert a relatively great amount of force against the desired location.

With continued reference to FIG. 4, housed within the sheath 22 is a first steering tendon 100 and a second steering tendon 102. The distal end 104 of the first steering tendon 100 is offset from the longitudinal centerline 98 of the sheath 22. In order to apply deflection force directly to the distal tip, the distal end 104 of the first steering tendon 100 is inserted into the bore 58 of the distal tip 32. The distal end 104 is then bonded into place with the resin 68. As will be discussed below in more detail, by placing the distal end 104 of the first steering tendon 100 at a location offset from the longitudinal centerline 98 of the sheath 22 and therefore proximate the inner surface 92 of the sheath 22, a relatively low amount of force applied to the first steering tendon 100 will generate a bending moment sufficient to deflect the distal-end region 24. To ensure a good bond between the resin 68 and the first steering tendon 100, and good anchoring of the tendon within the tip electrode, the distal end 104 of the first steering tendon is hook-shaped with a ball 106 disposed at the end. As will be discussed below in more detail, the distal end 108 (see FIGS. 4, 5, 10 and 13) of the second steering tendon 102 is attached within the distal-end region 24, proximate the inner surface 92 of the sheath 22, and proximal the attachment point of the first steering tendon 100. With reference to FIG. 1, the proximal end 110 of the first steering tendon 100 and the proximal end 112 of the second steering tendon 102 exit through the proximal end 52 of the sheath 22, and attach to a steering controller 114 within the handle 42. For clarification purposes, in following discussions, the term "attachment point" in relation to the distal end 104 of the first steering tendon 100 refers to the distal end of the first steering tendon being secured within the distal tip 32.

In some catheters that have a flat ribbon within the distal-end region and a steering tendon attached to a point proximal the distal tip within the distal-end region, undesirable deformation of the sheath can occur when the steering tendon is axially displaced in the proximal direction. More specifically, as the steering tendon is axially displaced in the proximal direction, the flat ribbon reduces the amount of axial displacement that the distal tip would normally experience. As a result, the portion of the sheath in the distal-end region proximal the attachment point compresses, thus causing that region of the sheath to wrinkle, and the portion of the sheath distal the attachment point stretches. Such deformation of the sheath can lead to fluid ingress beneath the catheter's band electrodes or can cause damage to internal wires or mechanical components. To reduce deformation of the sheath, the present catheter 20 includes a support system or compression cage 116 (FIGS. 4, 5, 10 and 13) within the distal-end region. The support system 116 functions to prevent the axial compression of the sheath 22 in the distal-end region 24 in the area proximal the attachment point of the second steering tendon 102, while still permitting deflection in the steering direction within that region. The prevention of axial compression in the distal-end region 24 in the area proximal the attachment point of the second steering tendon 102 coincidentally prevents the stretching of the distal-end region in the area distal the attachment point of the second steering tendon.

As shown in FIG. 4, the support system 116 includes a proximal end 118, a distal end 120, and a central lumen 122 there between. The support system 116 is preferably made from a resilient material, such as Nitinol, spring-temper austenitic stainless steel, or heat-treatable stainless steel so that it tends to return to a pre-established shape, such as straight. The proximal end 118 of the support system 116 is bonded to the distal end 82 of the eyelet 72, such as with epoxy. In one embodiment, an anchor band 124 (discussed in more detail below) is bonded to the distal end 120 of the support system 116 (FIGS. 4, 6 and 10), such as with epoxy. The flat ribbon 74 and tendons 100, 102 are housed within the support system.

With reference to FIGS. 7A–7E, various configurations of the support system or compression cage 116 are shown. In one configuration (FIG. 7A), the compression cage 116 includes a flat-wire coil 126 and two substantially longitudinal struts 128. The struts 128 are diametrically opposed from each other and are welded, soldered, brazed, adhered, or otherwise attached to some or all loops of the coil 126. In another configuration (FIG. 7B), the compression cage includes a round-wire coil 130 and two substantially longitudinal struts 132. The struts 132 are diametrically opposed from each other and are welded, soldered, brazed, adhered, or otherwise attached to some or all loops of the coil 130. In another configuration (FIGS. 7C and 7D), the compression cage includes a substantially tubular member 134 with an array of deep notches 136 that are diametrically opposed from each other. The material remaining between opposing notches 136 function as struts 138. In yet another configuration (FIG. 7E), the compression cage includes a linear array of rings 140 and two substantially longitudinal struts 142 that interconnect the rings. The struts 142 are diametrically opposed from each other and are welded, soldered, brazed, adhered, or otherwise attached to each of the rings 140.

The primary function of the struts 128, 132, 138, 142 is to provide columnar strength to the compression cage 116. When a tensile load is applied to a steering tendon 100, 102 to induce deflection of the distal-end region 24, the reaction to the load is carried by the struts 128, 132, 138, 142 within the compression cage 116 and transferred via the eyelet 72 into the relatively rigid proximal region 26. The compression cage deflects laterally most easily in a direction that is perpendicular to the plane in which a pair of opposing struts 128, 132, 138, 142 are located.

The support system 116 and anchor band 124 are independent of, but reside within, the central lumen 122 of the sheath 22 of the distal-end region 24. More specifically, the support system and anchor band are not attached directly to the sheath 22 of the distal-end region 24. In this configuration, a tensile load produced by axial translation of the second steering tendon 102 in the proximal direction causes the support system 116 and anchor band 124 to deflect laterally and push against the distal-end region 24, thereby causing the distal-end region to deflect. With the support system 116 and anchor band 124 being independent of the distal-end region 24 of the sheath 22, they do not cause the distal-end region to be either compressed or stretched.

In an alternate configuration, the support system 116 and anchor band 124 are attached to the inner surface 92 of the sheath 22 within the distal-end region 24, such as by melt-bonding, adhesives, or some equivalent mechanical means. As a result, a tensile load produced by axial translation of the second steering tendon 102 in the proximal direction causes the distal-end region 24 to compress in the area of the support system and to stretch in the area distal the support system. However, as previously mentioned, the reaction to the tensile load is carried by the struts 128, 132, 138, 142 within the support system 116 and is transferred via the eyelet 72 into the relatively rigid proximal region 26 of the sheath 22, thereby minimizing the associated compression and stretching of the distal-end region 24 of the sheath.

With reference to FIGS. 5 and 6, the anchor band 124 has two hollow cylindrical sections 143, 145 of different diameters with a step 152 between the cylindrical sections. The first cylindrical section 143 has a first inner surface 144 and a first outer surface 148, while the second cylindrical section 145 has a second inner surface 146 and second outer surface 150. The diameters of the first inner 144 and outer 148 surfaces are smaller than the diameters of the second inner 146 and outer 150 surfaces, respectively. The first outer surface 148 is inserted and bonded into the distal end 120 of the support system 116 prior to installation within the distal-end region 24. In one configuration, the support system 116 and anchor band 124 are attached to the inner surface 92 of the sheath 22. In this configuration, the second outer surface 150 of the anchor band 124 and the outer surface of the support system 116 are roughened, for example, by machining or by a micro-blasting process, in order to improve adhesion properties. The anchor band 124 is preferably made from a metallic material, such as stainless steel.

In this embodiment, the anchor band 124 is located proximal the most proximal band electrode 36. The distal end 108 of the second steering tendon 102 is welded, soldered, brazed, adhesively bonded, or otherwise attached to the first inner surface 144 of the anchor band 124. Such placement puts the distal end 108 of the second steering tendon 102 at a location offset from the centerline 98 of the sheath 22 and proximate the inner surface 92 of the sheath 22. As will be discussed below in more detail, by placing the distal end 108 of the second steering tendon 102 at a location offset from the centerline 98 of the sheath 22 and proximate the inner surface 92 of the sheath 22, a relatively low amount of force applied to the second steering tendon will generate a bending moment sufficient to deflect the distal-end region 24.

To attain optimal deflecting performance within the distal-end region 24, the deflecting direction of the compression cage 116 is parallelly aligned with the deflecting direction of the flat ribbon 74. As previously mentioned, the compression cage 114 deflects laterally most easily in a direction that is perpendicular to the plane in which a pair of opposing struts 128, 132, 138, 142 are located, and the flat ribbon 74 deflects most easily in a direction that is perpendicular to the width of the flat ribbon. A ribbon locator 154 is installed within the anchor band 124 (FIGS. 5 and 6) to ensure proper alignment between the pair of opposing struts 128, 132, 138, 142 and the flat ribbon 74 during catheter assembly, thereby aligning the easiest deflecting direction of the flat ribbon with the easiest deflecting direction of the support system 116. The ribbon locator 154 is oriented so that the edges 156 on the ribbon locator are parallel to the plane in which the struts 128, 132, 138, 142 are located and offset from the plane so that upon installation into the distal-end region 24, the edges 156 on the ribbon locator are adjacent to a face 158 on the flat ribbon 74. The ribbon locator 154 is welded, soldered, brazed, adhered, or otherwise attached to the first inner surface 144 of the anchor band 124. When installing the anchor band 124 and support system 116 within the distal-end region 24, the anchor band is oriented so that the edges 156 on the ribbon locator 154 are aligned to be parallel with the face 158 on the flat ribbon 74 on a side opposite the attachment point of the distal end 108 of the second steering tendon 102. The anchor band 124 and support system 116 are then bonded to the distal-end region 24 to fix the alignment of the flat ribbon 74 relative to the support system.

With the attachment of the support system 116 to the eyelet 72, torsional forces from the eyelet are transferred to the support system. The torsional forces in the support system are then transferred to the distal portion 120 of the support system 116 and into the ribbon locator 154. With the edges 156 of the ribbon locator 154 positioned adjacent to the face 158 on the flat ribbon 74, torsional forces from the ribbon locator are transferred to the flat ribbon, thus enhancing the torque transfer capabilities of the torque transfer system.

With reference to FIGS. 4, 5 and 10, a ribbon isolation sleeve 160 includes a proximal end 162, a distal end 164, and a central lumen 166 there between. The ribbon isolation sleeve 160 is preferably made from a tubular-shaped resilient material, such as Pebax™. It is also preferable that the ribbon isolation sleeve 160 include a wire coil 167 (FIG. 4) embedded therein, such as a stainless steel wire coil. The purpose of the ribbon isolation sleeve 160 is twofold: 1) to reduce wrinkling of the distal-end region 24 in the area between the anchor band 124 and the distal tip 32 during distal-tip steering, and 2) to reduce the likelihood of a short circuit between the flat ribbon 74 and the attachment points of the lead wires 40. The ribbon isolation sleeve 160 is housed within the distal-end region 24, with its proximal end 162 inserted and bonded into the second inner surface 146 of the anchor band 124, such as with cyanoacrylate. The lead wires 40 are routed distally through the ribbon isolation sleeve 160. The lead wires then wrap around the distal end 164 of the ribbon isolation sleeve 160 and are routed proximally towards the band electrodes 36.

With continued reference to FIG. 5, the first steering tendon 100 and the second steering tendon 102 are both housed within the sheath 22, are offset from the centerline 98 of the sheath, and are located proximate the inner surface 92 of the sheath. The first steering tendon 100 is attached at a location distal the second steering tendon 102. The general orientation of the steering tendons in the present embodiment is shown in the cross-sectional view of FIG. 8 where the first steering tendon 100 is located approximately 180° apart from the second steering tendon 102, on opposite sides of the flat ribbon 74. As shown in FIG. 9, having the steering tendons 100, 102 attached approximately 180° apart produces deflection profiles of the distal-end region 24 in opposite directions on opposite sides of the catheter 20. In this configuration, the catheter 20 steers in different directions when the steering tendons 100, 102 are axially displaced, thus the catheter is bidirectional.

With further reference to FIG. 5, the steering tendons 100, 102 may be formed from stainless steel wire having a diameter of approximately 0.2 mm. To reduce friction and thereby minimize the force required to steer the catheter 20, the two steering tendons 100, 102 are each enclosed within a respective sheath 168, 170. The sheaths 168, 170 cover substantially the entire length of the steering tendons 100, 102 and provide a relatively small clearance to permit the steering tendons to readily slide within the sheaths 168, 170. The sheaths include a tubular, polymeric material and are either coated or are formed of a low friction material, such as polytetrafluoroethylene (PTFE), known commercially as Teflon™.

The profile of the distal-end region 24 can be adjusted by manipulating the steering controller 114 (FIG. 1), which axially displaces either the first steering tendon 100 or the second steering tendon 102 in the proximal direction. Axially displacing a steering tendon in the proximal direction causes that steering tendon to experience greater tension. The tensile load is transferred to the steering tendon's 100, 102 distal attachment point, where other components of the catheter 20 structure react with a compressive load essentially equal in magnitude to the tensile load applied by the steering tendon. The tensile and compressive loads exist within the steering tendon 100, 102 and certain other components of the catheter structure, respectively, at all locations that are proximal to the tendon's distal attachment point. In addition, a bending moment is also present because the steering tendon's 100, 102 distal attachment point, by design, does not coincide with the longitudinal axis or centerline 98 of the catheter shaft 22.

More specifically, if tension is applied to the first steering tendon 100, it carries a tensile load to its distal attachment point, the tip electrode 34. At the attachment point, that tensile load is reacted to by an equivalent compressive load that is carried by several components within the catheter 20 structure, notably the flat ribbon 74, eyelet 72, and proximal region 26 of the sheath 22. One effect of the essentially equal but opposite axial forces is that the overall length of the catheter 20 structure somewhat shortens while the overall length of the first steering tendon 100 slightly lengthens. A substantial bending moment is also present at the attachment point because the two forces are deliberately offset from one another by the distance between the flat ribbon 74 and first steering tendon 100. The bending moment increases as the distance between the flat ribbon 74 and the first steering tendon 100 increases. The effect of the bending moment is to deflect the distal tip 32 toward the side to which the first steering tendon 100 is attached. Such deflection is balanced by the inherent bending stiffness of certain components of the catheter 20 structure, notably the flat ribbon 74, ribbon isolation sleeve 160, support system 116, and the distal-end region 24 of the sheath 22. As more tension is applied to the first steering tendon 100, the bending moment increases and thereby causes further deflection of the resisting components. Ultimately, the deflected shape 172 of the catheter's distal end resembles a circle (FIG. 9).

If tension is applied to the second steering tendon 102, it carries a tensile load to its distal attachment point, the anchor band 124. The tensile load at the attachment point is reacted to by an equivalent compressive load that is carried primarily by the support system 116, eyelet 74, and proximal region 26 of the sheath 22. The overall length of the compressive load carrying elements somewhat shortens while the overall length of the second steering tendon 102 somewhat lengthens. A substantial bending moment is generated at the second steering tendon's 102 distal attachment point, and its effect is to deflect the anchor band 124 toward the side to which the second steering tendon is attached. The deflection is balanced by the inherent bending stiffness of certain components of the catheter 20 structure, notably the support system 116, a portion of the flat ribbon 74, and the distal-end region 24 of the sheath 22. The ribbon isolation sleeve 160 and the distal portion of the flat ribbon 74 remain straight because the bending moment arises at the anchor band 124, which is located proximal the ribbon isolation sleeve. As more tension is applied to the second steering tendon 102, the resulting bending movement increases and thereby causes further deflection of the resisting components. Ultimately, the deflected shape 174 of the catheter's distal end resembles a letter "U" (FIG. 9).

The bending or deflection profiles 172, 174 (FIG. 9) of the catheter are somewhat asymmetric, a result of the axial displacement between the distal end mounting locations of the steering tendons 100, 102. The degree of difference in the deflection profiles 102, 104 depends upon the location of the attachment point of the distal end 108 of the second steering tendon 102 in comparison to the first steering tendon 100. Thus, the steering profiles can be altered by changing the location of the attachment point of the distal end 108 of the second steering tendon 102.

The components within the catheter that experience steering deflection are designed accordingly. For example, the flat ribbon 74 is relatively wide and thin and made of a highly resilient material so it will easily bend in one plane and will recover elastically after extreme deflection. Similarly, the steering tendons 100, 102 possess a small diameter and are made of spring temper stainless steel. The support system 116, in a preferred embodiment, is slotted such that it may readily accommodate bending in a specific plane, and the slot pattern is purposely helical to provide additional stability during extreme deflections. Furthermore, the external dimensions of both the support system 116 and the ribbon isolation sleeve 160 serve to substantially fill the distal-end region 24 of the sheath 22 to prevent it from buckling or otherwise experiencing nonuniform deformation during extreme steering deflections.

Although not shown, in an alternative configuration the distal ends 104, 108 of the steering tendons 100, 102 may both be attached to the distal tip 32 or to the proximal anchor band 124 such that the points of attachment are 1) axially identical along the length of the sheath and 2) angularly displaced from each other along the circumference of the inner surface of the sheath. Such placement of the steering tendons 100, 102 causes the deflection profiles of the catheter 20 to be identical although they will be angularly displaced from each other. For example, when the distal ends 104, 108 of the steering tendons 100, 102 are attached approximately 180° apart along the inner surface 92 of the sheath 22 as shown in FIG. 8, but are attached such that the distal ends are located at the same axial distance from the steering controller 114, the deflections will be symmetric and occur in opposite directions.

Figure 12:
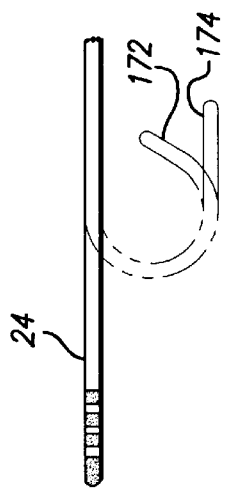
FIG. 12 is a schematic depicting the profiles that may be created within the distal-end region of the catheter of FIG. 10 when the first steering tendon and the second steering tendon are axially displaced in a proximal direction.
Figure 11:
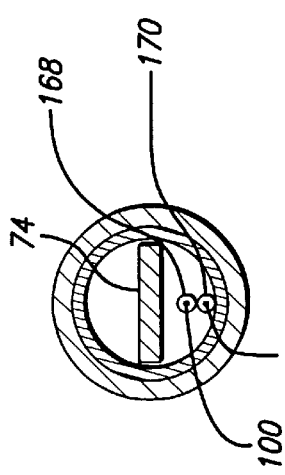
FIG. 11 is a cross-section view of the distal-end region depicting the steering tendons disposed approximately angularly aligned on the same side of the torque transfer system, taken along the line 11—11 from FIG. 10 with other items removed for clarity.

With reference to FIG. 10, an alternative embodiment of the catheter of FIG. 1 is depicted wherein both steering tendons 100, 102 are approximately angularly aligned on the same side of the flat ribbon 74. The first steering tendon 100 is attached at a location distal to that of the second steering tendon 102. The general orientation of the tendons 100, 102 is shown in the cross-sectional view of FIG. 11 where the first steering tendon 100 is located closer to the longitudinal centerline 98 of the catheter sheath 22 than the second steering tendon 102. As shown in FIG. 12, having the steering tendons 100, 102 approximately angularly aligned produces different deflection profiles on the same side of the catheter. In this configuration, the catheter 20 steers in the same direction when either steering tendon 100, 102 is axially displaced, thus the catheter deflection is unidirectional and asymmetric. However, the attachment of the first steering tendon 100 to the catheter sheath 22 at a position distal the second steering tendon 102 permits a greater curl to the deflected distal end, as shown in FIG. 12. The first dashed profile 172 is achieved through axial movement of the first steering tendon 100 alone while the second dashed profile 174 is achieved through axial movement of the second steering tendon 102 alone.

In FIG. 13, another embodiment is depicted where the anchor band 124 is removed and the distal end 108 of the second steering tendon 102 is welded, soldered, brazed, adhered, or otherwise attached directly to the inside surface 122 at the distal end 120 of the support system 116. Furthermore, the ribbon isolation sleeve 160 is bonded to the distal end 120 of the support system 116. In one embodiment, the support system 116 is independent of, but resides within, the central lumen 122 of the sheath 22 of the distal-end region 24. More specifically, the support system is not attached directly to the sheath 22 of the distal-end region 24. In this configuration, a tensile load produced by axial translation of the second steering tendon 102 in the proximal direction causes the support system 116 to deflect laterally and push against the distal-end region 24, thereby causing the distal-end region to deflect. With the support system 116 being independent of the distal-end region 24 of the sheath 22, it does not cause the distal-end region to be either compressed or stretched. In an alternate configuration, the support system 116 is attached to the inner surface 92 of the sheath 22 within the distal-end region 24, such as by melt-bonding, adhesives, or some equivalent mechanical means. As a result, a tensile load produced by axial translation of the second steering tendon 102 in the proximal direction causes the distal-end region 24 to compress in the area of the support system and to stretch in the area distal the support system. However, as previously mentioned, the reaction to the tensile load is carried by the struts 128, 132, 138, 142 within the support system 116 and is transferred via the eyelet 72 into the relatively rigid proximal region 26 of the sheath 22, thereby minimizing the associated compression and stretching of the distal-end region 24 of the sheath.

As shown in FIG. 13, in an alternative embodiment where the anchor band is not used, the ribbon locator 154 is welded, soldered, brazed, adhered, or otherwise attached to the inner surface 122 of the support system 116. The ribbon locator 154 is positioned so that the edges 156 of the ribbon locator are parallel to the pair of opposing struts 128, 132, 142, 138 (FIGS. 7A–7E). When installing the support system 116 within the distal-end region 24, the support system is oriented so that the edges 156 of the ribbon locator 154 are aligned to be parallel with the face 158 on the flat ribbon 74 on a side opposite the attachment point of the distal end 108 of the second steering tendon 102, and then bonded to the eyelet 72.

With reference to FIG. 14, in operation, a catheter 20 having bidirectional deflection configured in accordance with the invention is introduced into a biological site 176, such as the right atrium of the heart. During introduction, the catheter 20 is maintained in a substantially linear arrangement 178. While the distal end region 24 of the catheter 20 is being positioned near the area of target tissue 180 to be ablated, the distal-end region is deflected by pulling on the appropriate one of the steering tendons 100, 102, as previously described. Once the distal-end region 24 is adequately deflected 182 to establish contact between the tip electrode 34 and the area of target tissue 180, ablation energy is applied through the tip electrode. If the target tissue 180 comprises a linear segment, the catheter 20 is pulled in the proximal direction during the application of ablation energy to produce a lesion having length, as opposed to only a spot lesion.

Because the location of the attachment point of the first steering tendon 100 to the catheter sheath 22 is more distal than that of the second steering tendon 102 (see FIGS. 5 and 10), for an equal distance of axial translation of the steering tendons the first deflection profile 172 (see FIGS. 9 and 12) does not move the tip electrode 34 as far from the centerline 98 of a non-deflected catheter as does the second deflection profile 174. Also, the first deflection profile 172 may permit more force to be applied to the target site. Therefore, referring to FIG. 14, in instances where the target tissue 180 is located within a compact cavity within the patient, or a relatively higher amount of force is to be applied to the target tissue, it may be desirable to utilize the first deflection profile 172 of the catheter 20. Conversely, where the target tissue 180 is located within a more open cavity within the patient, or a relatively lower amount of force is to be applied to the target tissue, it may be desirable to utilize the second deflection profile 174 of the catheter 20. Hence, because of its ability to be configured with different distal end deflection profiles 172, 174, the catheter 20 of the present invention may be used to form multiple lesions in different environments within a patient without the need of multiple catheters.

It will be apparent from the foregoing that, while particular forms of the invention have been illustrated and described, various modifications can be made without departing from the spirit and scope of the invention. For instance, the present invention describes a steerable catheter that comprises two steering tendons. However, the torque transfer system and support system described herein can also be applied to catheters with only one steering tendon or more than two steering tendons.

What is claimed is:

1. A catheter comprising:
    a sheath including a proximal region, a distal-end region, and a longitudinal centerline;
    at least one steering tendon housed within the sheath, the steering tendon having a first end attached to the distal-end region of the sheath, and a second end located at the proximal region of the sheath, wherein movement of the steering tendon in a proximal direction causes the sheath distal-end region to deflect; and
    a support system having a proximal end, a distal end and a lumen there between, the support system sized to fit within the distal-end region of the sheath and configured to deflect laterally relative to the centerline and to resist axial compression along the centerline;
    wherein the support system comprises a helical coil defining the lumen and at least one strut secured to one side of the coil throughout the length of the coil.

2. The catheter of claim 1 wherein the support system comprises a pair of struts secured to diametrically opposite sides of the coil.

3. The catheter of claim 1 wherein the support system is formed of a resiliently deformable, shape-memory material.

4. A catheter comprising:
    a sheath including a proximal region, a distal-end region, and a longitudinal centerline;
    at least one steering tendon housed within the sheath, the steering tendon having a first end attached to the distal-end region of the sheath, and a second end located at the proximal region of the sheath, wherein movement of the steering tendon in a proximal direction causes the sheath distal-end region to deflect; and
    a support system having a proximal end, a distal end and a lumen there between, the support system sized to fit within the distal-end region of the sheath and configured to deflect laterally relative to the centerline and to resist axial compression along the centerline;

wherein the support system comprises a linear array of hollow rings defining the lumen and at least one strut secured to one side of each of the rings.

5. The catheter of claim 4 wherein the support system comprises a pair of struts secured to diametrically opposite sides of each of the rings.

6. The catheter of claim 4 wherein the support system is formed of a resiliently deformable, shape-memory material.

7. A catheter comprising:
a sheath including a proximal region, a distal-end region, and a longitudinal centerline;
at least one steering tendon housed within the sheath, the steering tendon having a first end attached to the distal-end region of the sheath, and a second end located at the proximal region of the sheath, wherein movement of the steering tendon in a proximal direction causes the sheath distal-end region to deflect;
a support system having a proximal end, a distal end and a lumen there between, the support system sized to fit within the distal-end region of the sheath and configured to deflect laterally relative to the centerline and to resist axial compression along the centerline; and
a ribbon isolation sleeve having a proximal end coupled to the distal-end of the support system.

8. The catheter of claim 7 wherein the ribbon isolation sleeve is formed of a resiliently deformable material.

9. The catheter of claim 8 wherein the ribbon isolation sleeve further comprises a wire coil embedded within the material.

10. The catheter of claim 7 wherein the first end of the steering tendon is attached at a location offset from the centerline of the sheath.

11. A catheter comprising:
a sheath including a proximal region and a distal-end region;
a first steering tendon housed within the sheath, the first steering tendon having a first end attached to the distal-end region at a point proximate an inner surface of the sheath, and a second end exiting a proximal end of the sheath, wherein movement of the first steering tendon in a proximal direction causes the sheath distal-end region to deflect;
a second steering tendon housed within the sheath, the second steering tendon having a first end attached to the distal-end region at a point proximate the inner surface of the sheath and proximal the attachment point of the first steering tendon, and a second end exiting the proximal end of the sheath, wherein movement of the second steering tendon in the proximal direction causes the sheath distal-end region to deflect; and
a compression cage having a proximal end, a distal end and a lumen there between, the compression cage sized to fit within the distal-end region of the sheath and configured to deflect laterally and to support an axial load.

12. The catheter of claim 11 wherein the first end of the second steering tendon is coupled to the compression cage.

13. The catheter of claim 12 wherein the first end of the second steering tendon attaches to a distal portion of the compression cage.

14. The catheter of claim 11 wherein the catheter further comprises an anchor band attached to the distal end of the compression cage.

15. The catheter of claim 14 wherein the first end of the second steering tendon is attached to the anchor band.

16. The catheter of claim 11 further comprising a torque transfer system housed within the compression cage and adapted to transfer torsional forces from the proximal region of the sheath to the distal-end region of the sheath.

17. The catheter of claim 16 wherein the torque transfer system comprises an eyelet secured at the distal end of the proximal region of the sheath and the proximal end of the compression cage is secured to the eyelet.

18. The catheter of claim 17 wherein the torque transfer system further comprises a ribbon housed within the compression cage and configured to deflect therewith, the ribbon having a first end secured to the eyelet and a second end attached to the distal-end region of the sheath.

19. The catheter of claim 18 wherein the ribbon is positioned along the centerline of the distal-end region of the sheath.

20. The catheter of claim 18 wherein the ribbon is formed of a resiliently deformable, shape-memory material.

21. The catheter of claim 18 wherein the ribbon has a substantially rectangular cross-section.

22. The catheter of claim 18 wherein:
the compression cage is adapted to deflect in a direction;
the ribbon is adapted to deflect in a direction; and
the compression cage further comprises a ribbon locator, the ribbon locator being adapted to align the deflecting direction of the compression cage with the deflecting direction of the ribbon.

23. A catheter for use with biological tissue, the catheter comprising:
a sheath including a proximal region and a distal-end region;
at least one electrode located in the distal-end region for transferring energy to the biological tissue;
a first steering tendon housed within the sheath, the first steering tendon having a first end attached to the distal-end region at a point proximate an inner surface of the sheath, and a second end exiting a proximal end of the sheath, wherein movement of the first steering tendon in a proximal direction causes the sheath distal-end region to deflect;
a second steering tendon housed within the sheath, the second steering tendon having a first end attached to the distal-end region at a point proximate the inner surface of the sheath and proximal the attachment point of the first steering tendon, and a second end exiting the proximal end of the sheath, wherein movement of the second steering tendon in the proximal direction causes the sheath distal-end region to deflect;
a compression cage having a proximal end, a distal end and a lumen there between, the compression cage sized to fit within the distal-end region of the sheath and configured to deflect laterally therewith and to resist axial compression; and
a torque transfer system housed within the compression cage and adapted to transfer torsional forces from the proximal region of the sheath to the distal-end region of the sheath.

24. The catheter of claim 23 wherein the first steering tendon is secured within a distal tip of the sheath.

25. The catheter of claim 23 wherein the at least one electrode comprises:
a tip electrode located at the distal end of the sheath; and
the first steering tendon is secured within the tip electrode.

26. The catheter of claim 23 wherein the compression cage comprises:
a helical coil defining the lumen; and
at least one strut secured to one side of the coil along the length of the coil.

27. The catheter of claim 26 wherein:

the catheter further comprises an anchor band having a proximal end and a distal end with a central lumen there between;

the anchor band is housed within the distal-end region; and the proximal end of the anchor band is attached to the distal end of the compression cage.

28. The catheter of claim 27 wherein the first end of the second steering tendon is attached to the anchor band.

29. The catheter of claim 23 wherein:

the torque transfer system comprises an eyelet secured at the distal end of the proximal region of the sheath; and the proximal end of the compression cage is secured to the eyelet.

30. The catheter of claim 29 wherein the torque transfer system further comprises a ribbon housed within the compression cage and configured to deflect therewith, the ribbon having a first end secured within the eyelet and a second end attached to the distal-end region of the sheath.

31. The catheter of claim 30 wherein:

the compression cage is adapted to deflect in a direction;

the ribbon is adapted to deflect in a direction; and the compression cage further comprises a ribbon locator, the ribbon locator being adapted to align the deflecting direction of the compression cage with the deflecting direction of the ribbon.

32. The catheter of claim 1 wherein the first end of the steering tendon is attached at a location offset from the centerline of the sheath.

33. The catheter of claim 4 wherein the first end of the steering tendon is attached at a location offset from the centerline of the sheath.

* * * * *

UNITED STATES PATENT AND TRADEMARK OFFICE
CERTIFICATE OF CORRECTION

PATENT NO.    : 6,585,718 B2
DATED         : July 1, 2003
INVENTOR(S)   : Robert C. Hayzelden et al.

It is certified that error appears in the above-identified patent and that said Letters Patent is hereby corrected as shown below:

<u>Title page,</u>
Item [56] References Cited, U.S. PATENT DOCUMENTS, under U.S. PATENT DOCUMENTS, add the following:
-- 5,855,552    1/1999  Houser et al.
   5,855,560    1/1999  Idaomi et al.
   5,865,800    2/1999  Mirachi et al.
   5,882,333    3/1999  Schaer et al.
   5,891,088    4/1999  Thomson et al.
   5,893,885    4/1999  Webster, Jr.
   5,897,529    4/1999  Ponzi
   5,916,147    6/1999  Boury
   5,928,191    7/1999  Houser et al.
   5,944,689    8/1999  Houser et al.
   5,984,907    1/2000  McGee et al.
   6,022,343    2/2000  Johnson et al.
   6,012,499    1/2000  Balazs
   6,033 378    3/2000  Lindquist et al. --.

Signed and Sealed this

Seventh Day of October, 2003

JAMES E. ROGAN
*Director of the United States Patent and Trademark Office*